United States Patent [19]

Masters et al.

[11] Patent Number: 4,810,248

[45] Date of Patent: * Mar. 7, 1989

[54] SYRINGE WITH SAFETY SHEATH AND SAFETY NEEDLE CAP

[76] Inventors: Edwin J. Masters, 142 Autumn, Sikeston, Mo. 63801; Paul L. Ebaugh, 1553 Lexington, Cape Girardeau, Mo. 63701

[*] Notice: The portion of the term of this patent subsequent to Jul. 21, 2004 has been disclaimed.

[21] Appl. No.: 129,471

[22] Filed: Dec. 7, 1987

Related U.S. Application Data

[60] Continuation-in-part of Ser. No. 943,657, Dec. 12, 1986, Pat. No. 4,740,204, which is a division of Ser. No. 825,524, Feb. 3, 1986, Pat. No. 4,654,034.

[51] Int. Cl.$^4$ .............................................. A61M 5/32
[52] U.S. Cl. .................................... 604/192; 604/263; 604/198
[58] Field of Search ................. 604/198, 192, 187, 263

[56] References Cited

U.S. PATENT DOCUMENTS

| | | |
|---|---|---|
| 1,179,560 | 4/1916 | Reed . |
| 2,539,510 | 1/1951 | Friden . |
| 2,571,653 | 10/1951 | Bastien . |
| 3,021,942 | 2/1962 | Hamilton ............................... 206/43 |
| 3,487,834 | 1/1970 | Smith, Jr. et al. ............... 640/197 X |
| 3,780,734 | 12/1973 | Wulff . |
| 3,890,971 | 6/1975 | Leeson et al. .................... 128/218 R |
| 3,893,608 | 7/1975 | Koenig ..................................... 225/1 |
| 4,373,526 | 2/1983 | Kling ..................................... 604/198 |
| 4,425,120 | 1/1984 | Sampson et al. ..................... 604/198 |
| 4,559,042 | 12/1985 | Votel ..................................... 604/192 |
| 4,631,057 | 12/1986 | Mitchell ............................... 604/198 |
| 4,645,034 | 3/1987 | Masters et al. ...................... 604/198 |
| 4,681,567 | 7/1987 | Masters et al. ...................... 604/198 |

FOREIGN PATENT DOCUMENTS 210267 1/1957 Australia .

OTHER PUBLICATIONS

PCT/US85/00003, Sumner, Syringe Needle Sheath and Shield, 02/12/84.
Sumner, Needlecaps to Prevent Needlestick Injuries, Infection Control, vol. 6, No. 12, p. 495 (1985).

Primary Examiner—John D. Yasko
Attorney, Agent, or Firm—Rogers, Howell, Moore & Haferkamp

[57] ABSTRACT

An improved syringe having a combined safety sheath and needle cap. The syringe is of the type comprising a barrel having a needle extending from the lower end. The sheath is slideably mounted on the barrel between a retracted position and an extended position, to visually indicate when the syringe has been used when the sheath is in the extended position, with means for locking the sheath in the extended position. A needle cap is provided for removal from the needle during use and for the possibility of recapping after use. The improved syringe further comprises a knob extending outwardly from the barrel near the lower end. The sheath has a slot for receiving the knob, the slot having tabs for releasably retaining the sheath in its retracted position releasable upon downward pressure applied to the sheath, and tabs for lockingly engaging the knob to lock the sheath in the extended position. The needle cap comprises a generally cylindrical, hollow tubular body section having a closed first end and an open second end for receiving the needle, with a funnel-shaped lip surrounding the open end and projecting radially and axially outwardly to channel needles into the open end and protect the user's fingers when gripping the cap. The cap further comprising generally triangular-shaped radial splines which extend between the body and the lip. The cap may also comprise a disk-shaped guard projecting radially from the body intermediate the ends or a funnel-shaped guard opening toward the open end and projecting from the body intermediate the ends.

28 Claims, 1 Drawing Sheet

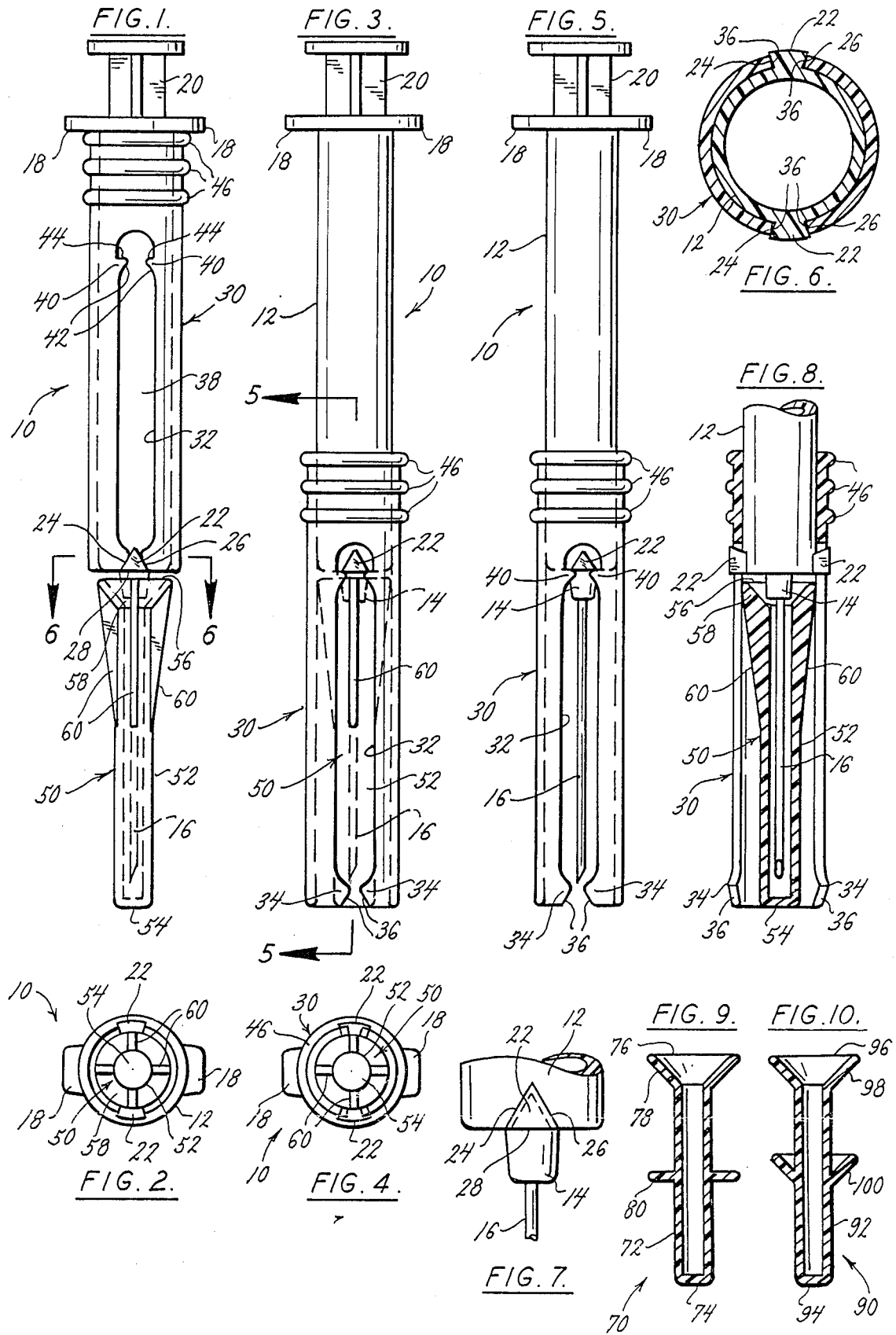

SYRINGE WITH SAFETY SHEATH AND SAFETY NEEDLE CAP

The present application is a continuation-in-part of applicants' prior application Ser. No. 06/943,657 filed on Dec. 12, 1986 now U.S. Pat. No. 4,740,204 which is a division of applicant's prior application Ser. No. 06/825,524 filed on Feb. 3, 1986 now U.S. Pat. No. 4,654,034.

BACKGROUND AND SUMMARY OF THE INVENTION

This invention relates to improvements in syringes and in particular to a syringe having a safety sheath and safety needle cap for preventing both needlesticks and reuse of the syringe.

Hypodermic needles, for example those used for injections or for taking blood samples, are usually equipped with a removable cap that protects and helps keep the needle sterile. The cap is usually replaceable to cover the used, contaminated needle and prevent accidental needlesticks. However, accidental needlesticks during recapping have long been a problem. Because of tension, time pressure, or fatigue, needlesticks during recapping occur with alarming frequency despite frequent warnings to be careful, and they account for a significant percentage of accidental needlesticks. Eliminating recapping will not solve the problem because the uncapped needle is so dangerous. Indeed, a large number of accidental needlesticks are caused by uncapped needles found in beds, on floors, or in garbage cans. Even where there is a no recapping policy, the needles are often recapped because of these dangers. Accidental needlesticks are serious because they can spread diseases, including hepatitis, venereal diseases, and of most recent concern: AIDS. A needlestick causes fear and anxiety in the victim. Both the victim and the patient may be subjected to a battery of expensive, timeconsuming tests. Accidental needlesticks during recapping can cost even a relatively small health care institution thousands of dollars annually. Even worse than the economic cost, however, is the transmission of disease.

For example, the victim of a needlestick from a needle contaminated by an AIDS patient must be repetitively tested after the accident. It is documented that after such a needlestick, the victim may test positive for exposure to the AIDS virus, even if the disease is not technically contracted. A positive test would cause great fear and anxiety in the victim, would seriously disrupt the victim's personal life, affect the insurability of the victim, and might even end the victim's ability to work in the health care industry.

Despite the very serious nature of the problem, and the severity of the consequences, the problem of accidental needlesticks has persisted for many years without any satisfactory solution. One approach to a solution is to modify the cap. For example, a recent article Sumner, "Needlecaps to Prevent Needlestick Injuries", INFECTION CONTROL (1985) Vol. 6, No. 12, p. 495, discusses the needlestick problem and discloses a needlecap with a small, wide angle funnel surrounding the cap opening. This funnel acts as both a guide and a shield. However, improvements to the cap do not totally eliminate the possibility of needlesticks. The action of bringing the cap and needle together still poses the threat of an accidental needlestick.

Another approach to a solution is to provide a sheath that can be slid down over the needle from behind, eliminating the risky action of bringing the cap and needle together. Various sheath devices have been patented, for example those disclosed in U.S. Pat. Nos. 4,425,120, 3,780,734, and 2,571,654. However, these devices were too complicated and very difficult to manufacture, and have never been widely available.

Still another approach to a solution has been to provide a syringe having both a needle cap and a sheath. This combination is shown in U.S. Pat. No. 4,425,120. However, the needle cap of this device is a conventional needle cap and it offered no protection against a needlestick when recapping the syringe. Furthermore, the sheath of this device was too complicated and very difficult to use.

This invention addresses the limited effectiveness of policy changes such as the "no recapping" policy adopted by the CDC. In a study reported in the Jan. 19, 1986 issue of HOSPITAL EMPLOYEE HEALTH, Bellevue Hospital Center in New York adopted new needle safety policies and procedures in 1983 which included a "no recapping" policy. In spite of a three month intensive promotional effort which included newsletters, memos, and an in-service educational program for the hospital staff, the incidence of needlestick injuries did not significantly change. Indeed, 13% of the injuries were from recapping needles in spite of the "no recapping" policy. Thus, this invention offers significant protection and additional safety for what some would call a common but improper use of the needle and syringe, i.e. recapping the needle.

Because of the problems with inadvertent needlesticks, numerous hospitals have adopted the "no recap" policy with regard to various needle caps. However, a safe method of recapping needles is advantageous for preventing needlesticks. Furthermore, despite contrary policy and instructions many of the medical personnel recap the needles anyway. The combination of the sheath and the cap of the present invention provides a synergistic affect that rebuts reasons against using either the cap or the sheath individually without the other. Thus, safety is increased for the common usages of the needle and syringe, which has repeatedly been shown to include recapping and disposal without recapping, regardless of policy.

The present invention features the combination of a special needle cap which can fit within a special sheath slidably mounted to the barrel of a syringe. The needle cap is sized to fit about the needle to prevent it from sticking into another. The sheath used in combination with the cap is slidably mounted over the barrel of the syringe. The sheath can be locked in a retracted position in which the needle cap extends beyond the sheath. The sheath can be moved to an extended position relative to the barrel. In being so extended, the sheath slides about the cap so that the cap is contained within the sheath. The sheath can be locked relative to the barrel in both the retracted and extended positions.

In use, the sheath can be mounted to the barrel in the retracted position. The cap can be mounted to the syringe to cover the needle. The cap can then be removed so that the syringe can be grasped and the needle used to inject the syringe contents into a patient. After the needle is removed from the patient, the sheath can be moved to the extended position and locked so that the sheath extends beyond the tip of the needle. This prevents inadvertent needlesticks.

Then, with the sheath extended, the cap can be moved to fit about the needle. The cap is inserted within the sheath with the cap's open end about the needle tip. The cap is moved into the sheath to completely fit about the needle, and be attached to the syringe, or to the sheath, and held in the capping position.

With the sheath extended in such fashion, one can observe that the syringe has been used even when the needle is capped. Thus, any reuse of this needle is prevented. With the recapping performed while the sheath is in the extended position, there is extra protection against a needlestick, since the cap can be moved toward the needle with the sheath guarding the operator's hands from the needle. Further, when the cap is remounted, the extended sheath blocks any inadvertent forces that otherwise might be directed against the cap to dislodge it from the syringe.

The inventors herein have developed the combination of a syringe with a safety sheath and a safety needle cap that reduces the possibility of needlesticks during recapping of the syringe after use. The combination of the sheath and cap also helps prevent needlesticks caused by needles found in beds, on floors, or in garbage cans. The safety sheath serves as both a guard to shield the needle during recapping and a visual indicator to show when the syringe has been used. There are some environments which require that a syringe be used only once and then disposed. The syringe of this invention could be effectively used in these environments.

In an embodiment of the invention, the syringe has at least one knob projecting outwardly from the barrel. The sheath also has at least one longitudinal slot for receiving the knob. The slot has a first set of opposing tabs projecting into the slot, the lower faces of which engage the top of the knob to retain the sheath in its retracted position. The lower faces of the first set of tabs are angled. These angled lower faces force the tabs apart to clear the knob when the sheath is forced downwardly against the knob. The slot also has a second set of opposing tabs projecting into the slot above the first set. The second set of tabs have angled lower faces and flat upper faces that form a shoulder. The angled lower faces force the tabs apart to clear the knob when the sheath is forced downwardly against the knob. The tabs resiliently snap back after clearing the knob, and the shoulders formed by the upper faces of the tabs engage the bottom surface of the knob and lock the sheath in the extended position.

The sheath is retained in its retracted position relative to the syringe until positive force is applied to overcome the resistance of the first set of tabs. The sheath is easily moved to its extended position by simply pushing the sheath downward. The sheath is easily locked in its extended position by simply pushing the sheath all the way down until the second set of tabs engage the knob. This positive locking action requires no special alignment or manipulation and it is easy to visually confirm.

The needle cap in an embodiment of the invention is a generally cylidrical, hollow tube closed at one end and open at the other end to receive the needle. The cap combined with the sheath provides advantages over the art. Further, the cap can have an outwardly facing funnel-shaped lip surrounding the open end to channel an errant needle into the opening and to protect the fingers gripping the cap, combined with means to space the fingers from the opening in the cap. These spacing means can be a plurality of radial splines extending between the exterior wall of the cap and the funnel-shaped lip to support the lip and to keep the user's fingers spaced from the cap opening. Alternatively, or additionally, a guard may project radially from the cap intermediate the ends of the cap. This guard can serve as secondary protection.

The combination syringe of the present invention is of simple construction and will be easy and inexpensive to make and simple to use. The locking action is positive and visually confirmable and without any special manipulation that can be improperly done. The cap may be used on any of the needle structures presently in use including disposable syringes.

BRIEF DESCRIPTION OF THE DRAWINGS

FIG. 1 is a side elevation view of a syringe with the combination safety sheath and a safety needle cap constructed according to the principles of this invention, with the safety sheath in the retracted position and the safety needle cap installed on a hypodermic needle;

FIG. 2 is a bottom end view of the combination sheath, cap, and syringe as shown in FIG. 1;

FIG. 3 is a side elevation view of the syringe with cap, with the safety sheath in the extended position;

FIG. 4 is a bottom end view of the sheath, cap and syringe as shown in FIG. 3;

FIG. 5 is a partial side elevation view of the barrel of the syringe with the safety needle cap removed and with the safety sheath in the extended position;

FIG. 6 is a cross-sectional view of the syringe and sheath taken along the line 6—6 in FIG. 1;

FIG. 7 is a partial side elevation view of the barrel of the syringe with the safety sheath and the safety needle cap removed, showing a knob;

FIG. 8 is a partial cross-sectional view of the syringe with sheath and cap taken along the line 5—5 in FIG. 3;

FIG. 9 is a cross-sectional view of a second embodiment of a needle cap constructed according to the principles of this invention incorporating a disk-shaped guard; and FIG. 10 is a cross-sectional view of a third embodiment of a needle cap constructed according to the principles of this invention incorporating a funnel-shaped guard.

DETAILED DESCRIPTION OF THE PREFERRED EMBODIMENTS

The syringe with the combination safety sheath and safety needle cap constructed according to the principles of this invention is indicated generally as 10 in the drawings. The syringe 10 comprises a barrel portion 12 terminating in a tip 14 at the lower end. Gradations or indicia (not shown) may be provided on the barrel 12 to indicate the volume in the syringe 10. A hypodermic needle 16 is mounted to the tip 14. Two diametrically opposed fingergrips 18 project radially outwardly from the top of the barrel 12. A plunger 20 reciprocates in the barrel 12 to draw and expel substances in the barrel 12.

At least one knob 22 projects radially outwardly near the bottom of the barrel 12. There are preferably two diametrically opposed knobs, as best shown in FIGS. 2, 4, and 6. As shown in FIGS. 1, 3, 5, and 7, the knobs 22 are preferably triangularly shaped with one of the vertices pointed upwardly. The upwardly facing left and right sides 24 and 26 of the knobs 22 are beveled to face radially inwardly, as best shown in FIGS. 2 and 6. The downwardly facing side 28 of the knob 22 extends generally horizontally, perpendicular to the axis of the syringe 10.

A sheath 30 is mounted on the barrel 12. The sheath 30 is preferably made of a resilient, transparent plastic so it does not mask the gradations or indicia on the barrel 12. The sheath 30 is slideable between a retracted position, shown in FIG. 1, and an extended position, shown in FIGS. 3 and 5. The sheath 30 has a slot 32 to receive each knob 22 on the barrel 12. Thus, in the preferred embodiment there are two diametrically opposed slots 32 in the sheath 30 to accommodate the two knobs 12. The slots 32 extend upwardly from the bottom edge of the sheath 30. The slots 32 preferably extend through the thickness of the sheath 30.

A first pair of tabs 34 extend from opposite sides into each slot 32, near the lower end. The lower edges 36 of the tabs 34 are angled downwardly and are also beveled to face radially outwardly. The central section 38 of the slot 32 has generally parallel sides, and is sized to accommodate the knob 22. A second pair of tabs 40 extend from opposite sides into the slot 32, above the first pair of tabs 34 near the upper end of the slot 32. The lower edges 42 of the tabs 40 are angled downwardly, and the upper edges 44 of the tabs 40 extend generally horizontally to form shoulders perpendicular to the slot 32. A plurality of raised annular ribs 46 extend around the sheath 30 near the top to provide a grip to slide the sheath 30 relative to the barrel 12.

In FIG. 1, the sheath 30 is in its retracted position. As shown in FIG. 6, the inwardly beveled sides 24 and 26 of the knobs 22 engage the outwardly beveled edges 36 of the tabs 34, to retain the sheath 30 against the barrel 12. The engagement between the lower edges 36 of the tabs 34 and the edges 24 and 26 of the knob 22 helps to retain the sheath 30 in the retracted position. However, the angled edges 36 of the tabs 34 force the tabs 34 apart when the sheath 30 is forced against the knob 22. The resiliency of the material that the sheath 30 is constructed from, and the presence of the slots 32, permit the sheath 30 to flex sufficiently for the tabs 34 to clear the knob 22.

After the tabs 34 clear the knob 22, the sheath 30 slides freely downwardly until the tabs 40 engage the knob 22. The engagement between the tabs 40 and the knobs 22 resists further downward movement of the sheath 30. However, the angled lower edges 42 of the tabs 40 force the tabs 40 when the sheath 30 is forced against the knob 22. Again, the resiliency of the material and the presence of the slots 32 permit the sheath 30 to flex sufficiently for the tabs 40 to clear the knob 22. After the tabs 40 clear the knob 22, they resiliently snap back together, and the shoulders formed by the upper edges 44 of the tabs 40 engage the bottom side 28 of the knob 22 to lock the sheath 30 in its extended position. Thus locked, the sheath 30 cannot move upward from its extended position, and the sheath 30 blocks access to the needle 16, preventing an accidental needlestick or reuse of the syringe 10.

The safety needle cap indicated generally as 50 comprises a generally cylindrical, hollow tubular body section 52. The front end 54 of the cap 50 is closed. The rear end 56 of the cap 50 is open to receive the tip 14 and the needle 16 of the syringe 12. When the cap 50 is properly seated on the syringe 12, the cap 50 covers and frictionally engages the tip 14.

A funnel-shaped lip 58 surrounds the opening in the rear end 56 of the cap 50, projecting radially outwardly and rearwardly from the body section 52 so that the funnel tapers toward the opening. The lip 58 provides a large target for the needle 16 during recapping and the funnel-shape of the lip 58 helps channel the needle 16 into the cap 50. The lip 58 also serves to protect the fingers gripping the cap 50.

As shown in FIG. 1 and 8, generally triangular shaped radial splines 60 extend between the body 52 and the lip 58. The splines 60 help stiffen and strengthen the lip 58. The splines 58 also make it difficult to grip the cap 50 near the open end 56. The splines 60 thus help to space the user's fingers from the open end 56 of the cap 50, out of danger, and thereby reduce the chance for an accidental needlestick.

The lip 58 of the cap 50 can be sized or made sufficiently flexible so that the cap can be used on TUBEX (trademark) unit dose cartridges and inserted and removed from the syringe device. For this purpose the lip 58 would preferably be flexible and have a diameter of about 9 mm.

A second embodiment of a needle cap constructed according to the principles of this invention is indicated generally as 70 in FIG. 9. Cap 70 is generally similar to the cap 50, comprising a generally cylindrical, hollow tubular body section 72, having a closed front end 74 and an open rear end 76. A funnel-shaped lip 78 surrounds the opening in the rear end 76 of the cap 70. However, unlike the cap 50, the cap 70 has a disk-shaped guard 80 projecting radially from the body section 72 intermediate the ends. The guard 80 serves as a secondary protection if the needle misses the funnel-shaped lip 78 when the cap 70 is being reinserted over the needle 16 and the sheath 30 is in the retracted position. The guard 80 is positioned so that it is difficult to grip the cap 70 between the lip 8 and the guard 80.

A third embodiment of a needle cap constructed according to the principles of this invention is indicated generally as 90 in FIG. 10. Cap 90 is generally similar to the cap 50, comprising a generally cylindrical, hollow tubular body section 92, having a closed front end 94 and an open rear end 96. A funnel-shaped lip 98 surrounds the opening in the rear end 96 of the cap 90. However, unlike the cap 50, the cap 90 has a funnel-shaped guard 100 opening toward the open end 96, and projecting from the body section 92 intermediate the ends. The guard 100 serves as a secondary protection if the needle misses the funnel-shaped lip 98 when the cap 90 is being reinserted over the needle 16 and the sheath 30 is in the retracted position. The guard 100 is positioned so that it is difficult to grip the cap 90 between the lip 98 and the guard 100.

If desired, either the disk-shaped guard 80 or the funnel-shaped guard 100 could also be used in conjunction with the cap 30 having the radial splines 60. It shall also be noted that the diameters of the funnel-shaped lips 78 and 98, the disk-shaped guard 80, and the funnel-shaped guard 100 have smaller diameters than the sheath 30. This allows unrestricted movement of the sheath 30 when either of the caps 70 or 90 are installed over the needle 16.

OPERATION

The syringe 10 may be provided with the sheath 30 in its retracted position and the cap 50 as shown in FIG. 1. The cap 50 is removeable and helps to protect the needle 16 and keep it sterile. When the cap 50 is removed the syringe 10 can be used, for example to give an injection. To discourage further use of the syringe 10 and/or to protect against needlesticks the sheath 30 is grasped by the raised ribs 46, and urged downwardly. The downward force applied to the sheath 30 urges the tabs 34 against the knob 22. The angled edges 36 of the tabs 34 force the tabs 34 apart to clear the knob 22. Once the tabs 34 clear the knob 22, the sheath 30 slides freely downwardly until the tabs 40 engage the knob 22. Continued downward pressure forces the tabs 40 against the knob 22. The angled lower edges 42 of the tabs 40 force the tabs 40 apart to clear knob 22. Once the tabs 40 clear the knob 22, the tabs snap resiliently back, locking the sheath 30 in its extended position. The shoulders formed by the top edges 44 of the tabs 40 engage the bottom side 28 of the knob 22, preventing the sheath 30 from moving upward. Once the sheath 30 is locked in its extended position the needle is recapped with the cap 50. With the sheath 30 in the extended position before recapping, the needle 16 is surrounded by the sheath 30 guarding against needlesticks when recapping.

The lip 58 and splines 60, as well as the disc guard 80 or funnel guard 100 in the modifications of FIGS. 9 and 10, provide an added barrier of protection against needlesticks should for any reason the sheath 30 not remain surrounding the needle 16. Thus the present invention provides an extra margin of safety against misuse and harmful needlesticks.

With the safety cap recapped and the sheath in its extended position the syringe is nonreusable. Individuals will now be alerted that the syringe has been used and may now be contaminated. The syringe of the present invention can visually indicate when it has been used and appropriate disposal procedures may then be followed. Once the syringe has been disposed, the combined safety features protect against potential injury by having a sheath which protects the cap from being dislodged from the needle and a cap which covers the needle.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. An improved syringe of the type comprising a barrel having a needle extending from the lower end, the improvement comprising in combination:
   a sheath, means for slideably mounting the sheath on the barrel to be slideable between a retracted position relative to the barrel, and an extended position relative to the barrel;
   means for locking the sheath in the extended position; and
   a needle cap with means for being mounted about the needle for removal from the needle during use and for recapping after use; the cap being sized to fit substantially within the sheath when the sheath is in the extended position, the needle cap comprising a generally cylindrical hollow tubular body section, having a closed first end and an open second end for receiving the needle, a funnel-shaped lip surrounding the opening in the second end and projecting radially and axially from the second end, in combination with means for spacing the user's fingers from the second end of the cap.

2. The improved syringe of claim 1 wherein the sheath further comprises:
   at least one knob extending outwardly from the barrel near the lower end; and
   at least one longitudinal slot means in the sheath for receiving the knob, the slot means having means for releasably retaining the sheath in its retracted position, the releasable retaining means being releasable upon downward pressure applied to the sheath.

3. The improved syringe of claim 2 wherein the slot means is an open slot extending through the wall of the sheath for receiving the knob.

4. The improved syringe of claim 2 wherein the slot means is a longitudinal groove in the interior of the sheath for receiving the knob.

5. The improved syringe of claim 1 wherein the sheath has raised ribs at the upper end to aid in gripping the sheath.

6. The improved syringe of claim 1 wherein there are two knobs extending from the barrel at diametrically opposed locations, and wherein there are two slot means in the sheath, each slot means receiving one of the knobs.

7. The improved syringe of claim 2 wherein the knob is triangularly shaped, with one of the vertices oriented upwardly.

8. The improved syringe of claim 2 wherein the knob and the sheath have radially inwardly and outwardly beveled faces, respectively, that engage each other to retain the sheath against the barrel.

9. The improved syringe of claim 2 wherein the slot means extends upwardly from the lower end, the slot means having a first set of opposing tabs extending into the slot means near the lower end, the first set of tabs engaging the knob when the sheath is in the retracted position and releasably retaining the sheath in the retracted position, the first set of tabs having angled lowered faces, these angled lower faces forcing the tabs apart to clear the knob when forced downwardly against the knob; the slot further having a second set of opposing tabs extending into the slot above the first set of tabs, near the upper end of the slot, the second set of tabs having angled lower faces and flat upper faces that form a shoulder, these angled lower faces forcing the tabs apart to clear the knob when forced against the knob, the second set of tabs resiliently snapping back after clearing the knob, the shoulders and the upper end of the slot cooperating to trap the knob and lock the sheath in the extended position.

10. The improved syringe of claim 9 wherein the lower faces of the first set of tabs are beveled to face radially outwardly and wherein the knob has faces beveled to face inwardly, the beveled faces on the knob engaging the beveled faces of the tab and retaining the sheath against the barrel.

11. The improved syringe of claim 1 wherein the means for spacing the user's finger's from the second end of the cap comprises at least one longitudinally extending spline and the funnel-shaped lip on the exterior of the cap.

12. The improved syringe of claim 11 wherein there are four splines equally spaced about the circumference of the body section.

13. The improved syringe of claim 1 wherein the funnel-shaped lip is flexible.

14. The improved syringe of claim 13 wherein the diameter of the funnel-shaped lip is less than about 1 cm.

15. The improved syringe of claim 1 wherein the means for spacing the user's fingers from the second end of the cap comprises a guard extending from the body section intermediate the ends, the guard positioned sufficiently close to the funnel-shaped lip that the cap cannot be gripped between the guard and the lip.

16. The improved syringe of claim 15 wherein the guard is disk-shaped, extending radially from the body section.

17. The improved syringe of claim 15 wherein the guard is funnel-shaped, opening toward the open end in the cap.

18. An improved syringe of the type comprising a barrel having a needle extending from the lower end, the improvement comprising in combination:
  at least one knob extending outwardly from the barrel near the lower end;
  a sheath slidably mounted on the barrel and slidable between a retracted position relative to the barrel in which the sheath does not obstruct access to the needle and an extended position relative to the barrel;
  at least one longitudinal groove in the interior of the sheath for receiving the knob, the groove having first means for engaging the knob when the sheath is in the retracted position; means for releasing the engagement between the first engaging means and the knob upon downward pressure applied to the sheath; second means for engaging the knob when the sheath is in its extended position to lock the sheath in the extended position;
  a needle cap for removal from the needle during use and for recapping after use, the cap having means for being mounted about the needle of the type comprising a generally cylindrical hollow tubular body section, having a closed first end and an open second end for receiving the needle;
  a funnel-shaped lip surrounding the opening in the second end, and projecting radially and axially from the second end and sized to fit within the sheath, the cap having means for spacing the user's fingers from the second end of the cap.

19. The improved syringe of claim 18 wherein the knob has a sloped upper face; and wherein the first engaging means comprises a tab extending from the bottom of the groove into the groove near the lower end.

20. The improved syringe of claim 18 wherein the means for releasing the engagement between the first engaging means and the knob comprises a sloped surface on at least one of the tabs or the first engaging means.

21. The improved syringe of claim 18 wherein the second means for engaging the knob comprises a means for defining a shoulder generally perpendicular to the groove and means on the knob for engaging the shoulder.

22. The improved syringe of claim 18 wherein the means for spacing the user's fingers from the second end of the cap comprises at least one longitudinally extending spline and the funnel-shaped lip on the exterior of the caps 23. The improved syringe of claim 22 wherein there are four splines equally spaced about the circumference of the body section.

24. The improved syringe of claim 18 wherein the funnel-shaped lip is flexible.

25. The improved syringe of claim 24 wherein the diameter of the funnel-shaped lip is less than about 1 cm.

26. The improved syringe of claim 18 wherein the means for spacing the user's fingers from the second end of the cap comprises a guard extending from the body section intermediate the ends, the guard positioned sufficiently close to the funnel-shaped lip that the cap cannot be gripped between the guard and the lip.

27. The improved syringe of claim 26 wherein the guard is disk-shaped, extending radially from the body section.

28. The improved syringe of claim 26 wherein the guard is funnel-shaped, opening toward the open end in the cap.

* * * * *